United States Patent [19]

Hemming et al.

[11] Patent Number: 5,039,949
[45] Date of Patent: Aug. 13, 1991

[54] RF ABSORBER TEST SYSTEM

[76] Inventors: Leland H. Hemming, 13329 Canyon Back La., Poway, Calif. 92064; Gabriel A. Sanchez, P.O. Box W, Santee, Calif. 92071-0618

[21] Appl. No.: 56,393

[22] Filed: Jun. 1, 1987

[51] Int. Cl.$^5$ .......................................... G01N 22/00
[52] U.S. Cl. ................................. 324/646; 324/645; 343/703
[58] Field of Search ............... 324/58 C, 58.5 C, 58 B, 324/95, 96, 633, 636, 637, 645, 646; 343/703, 872

[56] References Cited

U.S. PATENT DOCUMENTS 3,113,267  12/1963  Oh ..................................... 324/58 B

OTHER PUBLICATIONS

Hemming et al., The RF Absorber Horn Test System, 10-1986, pp. 145-149.
Constantine A. Balanis, "Antenna Theory Analysis and Design", 12-1982, pp. 705 & 706.

*Primary Examiner*—Kenneth Wieder
*Assistant Examiner*—Jack B. Harvey
*Attorney, Agent, or Firm*—Ralph Branscomb

[57] ABSTRACT

A method of testing the reflectivity of RF absorber materials utilizes an elongated chamber lined with RF absorber material and having a source antenna at one end, with the other end terminating in either a "short circuit", or a piece of RF absorber material which is to be tested. A probe antenna is moved along the axis of the chamber and the standing wave created by the source antenna and the reflection from the other end is recorded, first with the short circuit condition, and then with the test sample in place, and the results are compared to yield a figure for the reflectivity of the test sample.

5 Claims, 3 Drawing Sheets

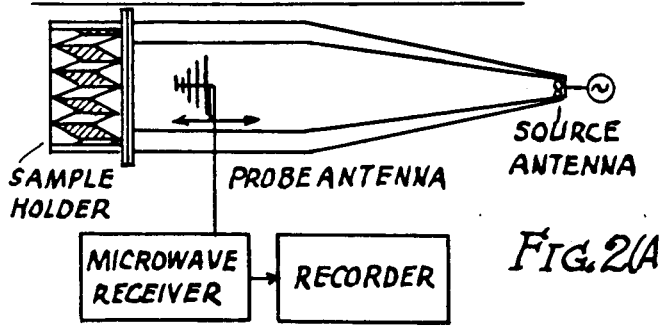
FIG. 1
RF ABSORBER HORN TEST SYSTEM
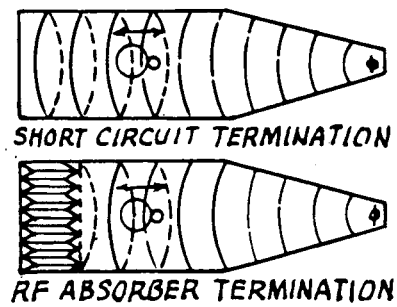
FIG. 2(A) SHORT CIRCUIT TERMINATION
FIG. 2(B) RF ABSORBER TERMINATION
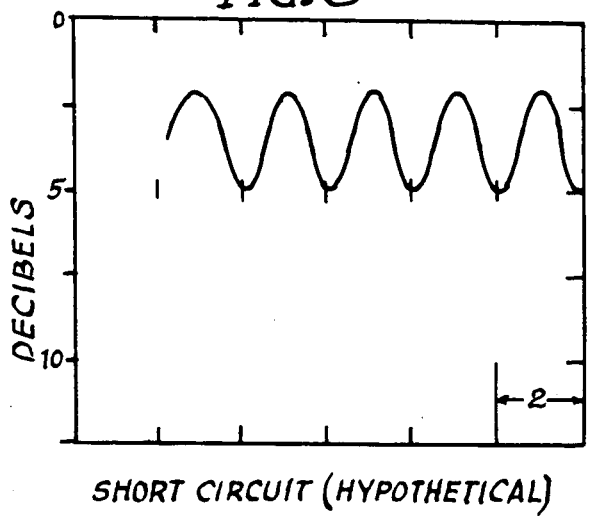
FIG. 3 SHORT CIRCUIT (HYPOTHETICAL)
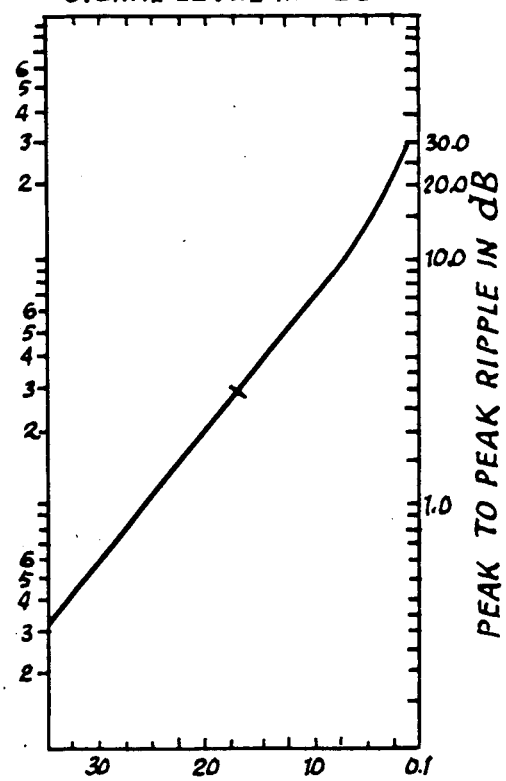
FIG. 4 SIGNAL LEVEL IN -dB
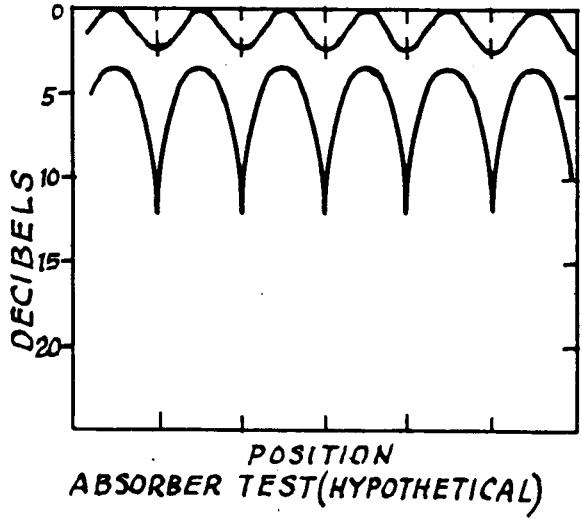
FIG. 5 ABSORBER TEST (HYPOTHETICAL)

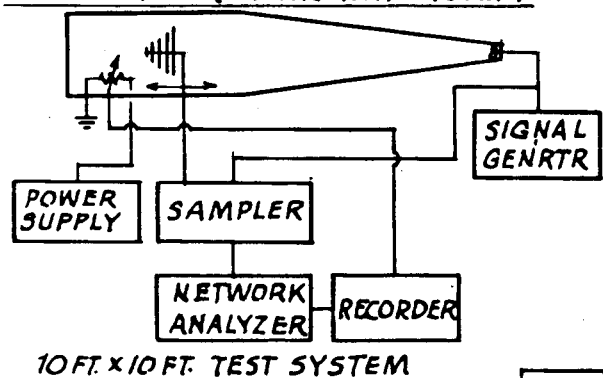
FIG. 6
SMALL CHAMBER INSTRUMENT SYSTEM
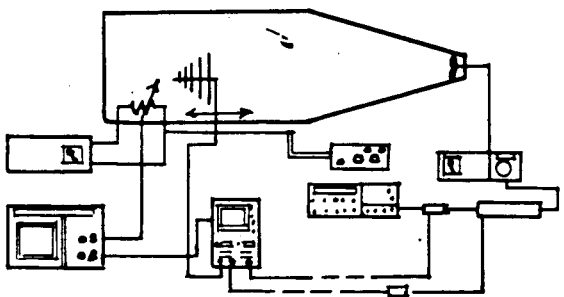
FIG. 7
10 FT. X 10 FT. TEST SYSTEM
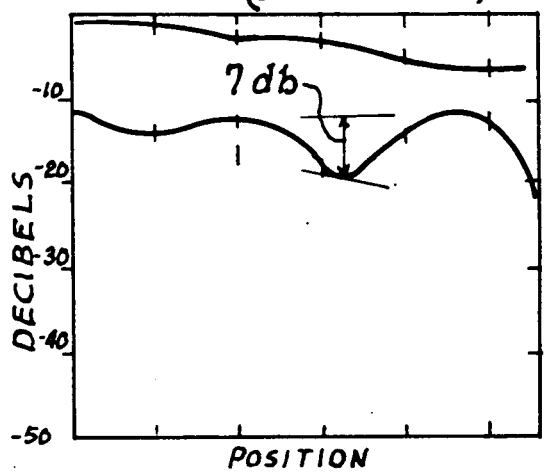
FIG. 8
TRIAL #1 (SHORT CIRCUIT)
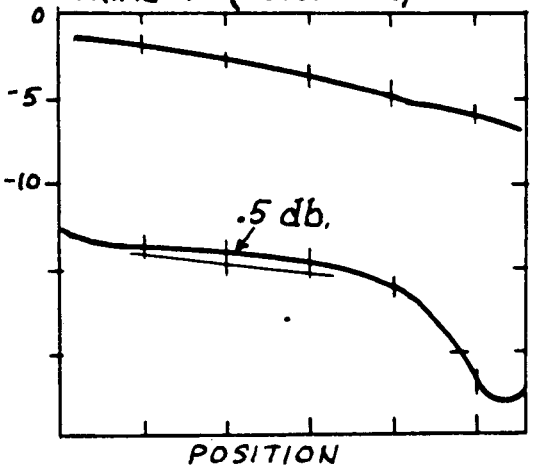
FIG. 9
TRIAL #1 (ABSORBER)
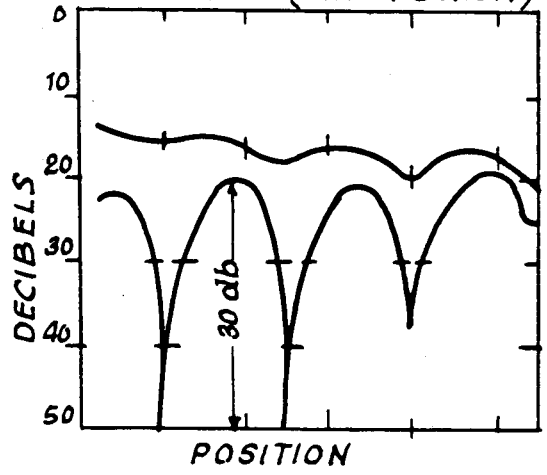
FIG. 10
TRIAL #2 (SHORT CIRCUIT)
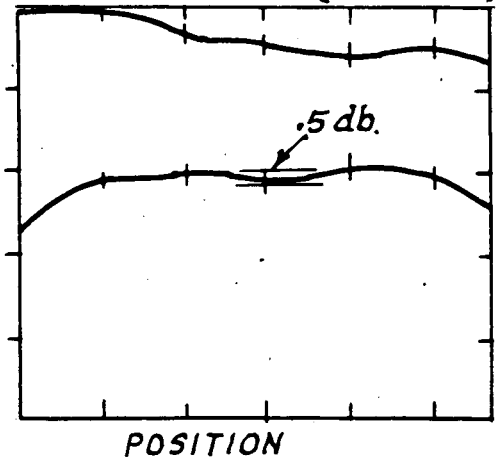
FIG. 11 TRIAL #2 (ABSORBER)

TRIAL #3 (SHORT CIRCUIT)

TRIAL #3 (ABSORBER)

TRIAL #4 (SHORT CIRCUIT)

TRIAL #4 (ABSORBER)

RF ABSORBER TEST SYSTEM

BACKGROUND OF THE INVENTION

The invention is in the field of anechoic chambers in general, and particularly relates to testing the efficacy of the radio frequency absorber material that is used to line anechoic chambers.

In the past, there are two methods which have been used to test the RF absorbing material. The most common method is the Naval Research Lab Technique, the NRL Arch Test System, which consists of the use of two relatively high gain antennas (16 dBi minimum standard gain horns) mounted above a metal reference plate. A measurement is made, and then a sample out of absorber material to be measured is then put over the reference plate. In order to measure a −40/50 dB return loss, the sample size must be at least 6 wave lengths on a side. For this reason, when testing with wavelengths below one GHz, this technique becomes difficult to implement.

Below the one GHz a waveguide method has been used with limited success. This technique involves placing the absorbers on a sliding mechanism which moves in and out of the mouth of a large waveguide. Waveguides operating as low as 120 MHz have been constructed.

However, due to the very nature of the construction restraints inherent in the building of the waveguide test fixture, there are many uncertainties built into the system. A major source of error is due to the required transition from a flared rectangular horn section to the square, straight-sided section of the waveguide. If the transition between the flared section and the straight section is not very precisely controlled, large errors are introduced into the measurements. Because the absorber reflectivity can be of the same order of magnitude (45–55 dB) as transition reflections, measurement errors up to five dB are common.

In an attempt to overcome this problem, sliding load techniques have been employed in which the absorber is mounted on a mechanically movable wall which moves through the waveguide. However, in order to measure low operating frequencies the wall must be on the order of 4 feet high and 10 feed wide, so large that difficulties are encountered in moving the wall smoothly through the waveguide. Additionally, operating frequencies are limited to standard guide bandwidths.

SUMMARY OF THE INVENTION

The instant invention substantially solves the above described problems, although the method still requires a minimum size of the sample RF absorber material of one wave length square. The test system utilizes a straight-sided square chamber, a minimum of one wave length on a side and 1.5 wave lengths long, which is lined with a high loss edge absorber material. Connected to and feeding this square section is a tapered horn approximately 2 wave lengths long, also lined with high loss absorber material.

The chamber has a track down the center, and a movable carriage system which rides on the track mounts a broad band directional probe antenna. One end of the chamber is the narrower end of the tapered horn, and a low gain, broadband antenna is mounted at this end. The other end of the chamber terminates in a "short circuit", a flat end which reflect most of the RF energy which impinges upon it.

In order to test a particular sample of RF absorber material, first the directional probe antenna is moved along the track in its carriage, directed at the short circuit end of the test chamber, while the broadband source antenna is being driven in the tapered horn section of the chamber. The probe antenna picks up a standing wave comprising the RF radiation from the source antenna and the reflected radiation from the short circuit. As the probe antenna sweeps, the amplitude of this standing wave is recorded, to produce a ripple line on a graph. The peak-to-peak amplitude of the ripple is then measured, and from this information, the level of the amplitude level of the reflected signal is calculated by utilizing a standard chart.

The same technique is duplicated, but this time with the radio frequency of probing material in place at the end of the chamber previously terminating in a short circuit. The ripple is again recorded, the peak-to-peak amplitude measured, and again the reflected signal is calculated in decibels. The decibel reflectivity from the short circuit condition and the absorber termination are then added together to produce a decibel figure for the reflectivity of the test sample of the absorber material.

BRIEF DESCRIPTION OF THE DRAWINGS

FIG. 1 illustrates diagrammatically the basic arrangement for the test method;

FIG. 2 is a diagrammatic illustration of the sweeping of the probe antenna inside the test chamber, with FIG. 2A representing the short circuit condition 2B representing the absorber arrangement;

FIG. 3 is a hypothetical result expected from recording the output from the probe antenna with a short circuit condition;

FIG. 4 is a standard chart utilized for converting the peak-to-peak ripple magnitude to the signal level reflected from the end of the chamber;

FIG. 5 is the hypothetical result of a test of a piece of absorber material, with the main trace being identical to that of FIG. 3 except that the absorber material is in place rather than the short circuit;

FIG. 6 is a schematic of one set-up for the test system;

FIG. 7 is an arrangement somewhat different from that of FIG. 6 for testing; and, FIGS. 8 through 15 are the actual test results from four different trials of the system, with the first graph of each pair representing the short circuit condition and the second graph of each pair representing the test of the absorber material.

DETAILED DESCRIPTION OF THE PREFERRED EMBODIMENT

Figure 12:
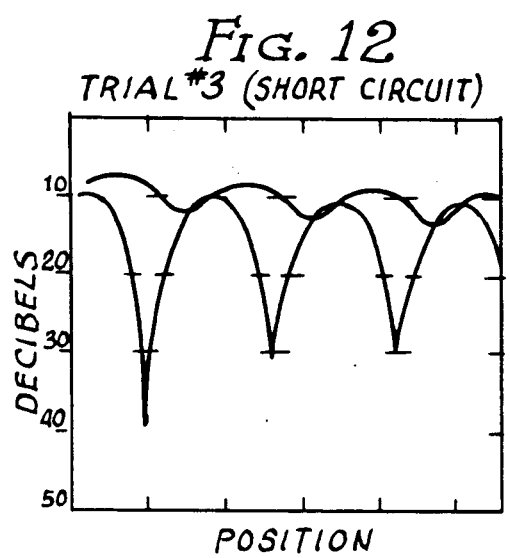
Figure 13:
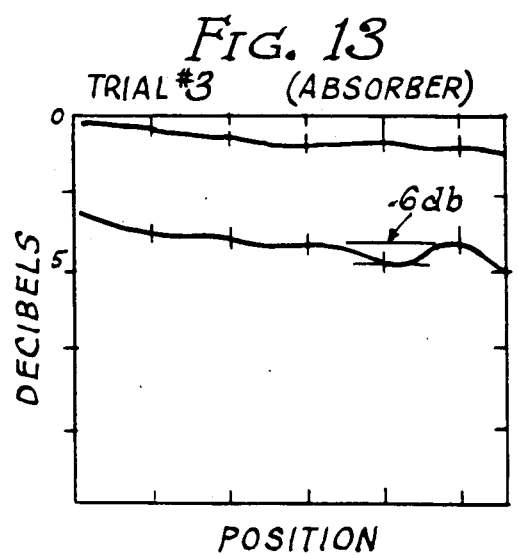

The RF Absorber Horn Test System facilitates the measurement of high performance RF anechoic chamber absorbers over the 100 MHz to 18 GHz frequency range. Absorber reflectivity measurements as low as −50 dB are possible at normal incidence with practical sized samples.

The test system consists of a square horn lined with high loss edge absorber material driven by a tapered horn section which is lined with flat high loss absorber. The tapered section is fed by an electrically small source antenna and the square section adjoining the tapered section houses a directional probe antenna which is moved longitudinally along the axis of the horn to detect the standing wave created by the electromagnetic wave reflecting from the test sample mounted in the end of the square horn and the uniform incident wave formed by the tapered horn at the source end.

The operation of the RF Absorber Horn Test System can be understood by considering FIG. 2(a) and 2(b).

The horn is first terminated in a short circuit. The uniform wave originating from the tapered end is reflected from the termination of the horn and a standing wave pattern is set up in the test region by the superposition of the incident and reflected waves. As the probe antenna is moved through the field, the standing wave pattern is recorded.

The recorded pattern is a resultant of several factors. First, if the frequency of operation is low, the period of the pattern will be long, even longer than in free space, since the horn will behave somewhat like a waveguide where the horn dimensions are on the order of a wavelength. Where the horn is large in terms of wavelength, the propagation conditions approach free space and the period of the ripple will approach $\lambda/2$ in free space.

Second, the observed ripple or SWR (Standing wave Ratio) will be a function of the front-to-back (F/B) ratio of the probe antenna. If the antenna had an infinite F/B ratio, then it would discriminate against the incident wave and would only record the reflected wave. This would result in a flat, level recording, neglecting propagation losses. If the probe antenna had an omni pattern or unity F/B ratio, then a very large ripple would result, 6 dB to $-\infty$, if the incident and reflected waves were identical in magnitude. The actual measured ripple will lie between these two extremes because of the finite front-to-back ratio of the probe antenna and the propagation losses.

Third, the propagation losses in the absorber-lined horn are not the same as experienced in free space due to the lossy walls, and at the low frequency end a waveguide like operation is experienced. The loss slope measured along the chamber axis is a complex function and can only be determined by experiment. When the probe antenna is pointed toward the short circuit, the recorded pattern will be the difference between the F/B ratio of the probe antenna and the differential loss between the incident and reflected waves. This has been designated as the effective F/B ratio. Having recorded the short circuit termination with the probe antenna pointed toward the short, the absorber to be evaluated is installed and the measurement repeated.

Referring to FIG. 2(b), the signal recorded will be a function of the absorber reflectivity and the effective front-to-back ratio of the probe antenna.

The usual case is that the absorber reflectivity is lower than the F/B ratio, and the result is a drop in the level of the energy received by the probe antenna equal to the effective F/B ratio. The absorber performance is found by evaluating the peak-to-peak ripple of the two traces and adding the two reflected energy levels together. Again, the effective F/B ratio is the resultant of the probe F/B ratio modulated by the propagation losses of the incident and reflected waves in the test region of the horn when the probe antenna is pointed toward the load end of the horn.

To illustrate the operation of the RF Absorber Horn Test System, consider operation under the following conditions:
Large Horn Test System: $10' \times 10' \times 35'$
Frequency of operation: 400 MHz
Assumed differential loss between the incident and reflected waves: 3 dB.
Probe F/B ratio: 20 dB.
Absorber reflectivity: 0 to $-40$ dB.

Case I: 0 dB, or Short Circuited Condition

With the probe antenna facing the short circuit and moved 10 feet through the test region, the ripple recorded will be the difference between the F/B ratio and the differential loss between the incident and reflected waves. For the assumed conditions this would be 17 dB. This value is known as the effective F/B ratio of the probe antenna. The period will be longer than the free space half wavelength (The exact amount is not known and can only be determined by experiment.). The expected curve that would be recorded is illustrated in FIG. 3. Note that the peak-to-peak ripple is 2.6 dB, which from FIG. 4 indicates a reflected signal of $-17$ dB.

Case 11: 10 dB Absorber Reflectivity.

Repeating the same arrangement in Case, the recorded pattern would be as shown in FIG. 5. Since less energy is available from the end termination, the signal level will drop and the peak-to-peak ripple will increase, since the differential loss between the F/B ratio and the reflected wave is only 7 dB. The peak-to-peak ripple is 8.4 dB. Thus the reflectivity of the absorber is found by noting that the signal level dropped, but less than the F/B ratio measured under the short circuit conditions, therefore the absorber performance is the difference between the reflected level from the short circuit and the CASE III: 17 dB Absorber Reflectivity In this case, the effective F/B ratio and the absorber reflectivity are equal, resulting in the effective incident and reflected signal levels being equal. The result is that the average signal level drops 17 dB and the ripple magnitude varies between 6 dB and $\infty -$. To accurately record this case, the dynamic range of the test system would have to be on the order of 67 dB, referenced from the incident level condition, i.e., with the probe antenna pointed toward the source antenna.

CASE IV: 30 dB Absorber Reflectivity

This situation is the preferred arrangement since the signal measured is below the F/B ratio of the probe antenna. The result is that the average pattern level will be 17 dB below the initial short circuit conditions, and the ripple will be proportional to the difference between the effective F/B ratio and the absorber reflectivity or $-13$ dB. The peak-to-peak ripple recorded would be 4.2 dB. The absorber reflectivity is the SUM of the measured reflected signals.

CASE V: 40 dB Absorber Reflectivity

The measured ripple is found to be 1.3 dB, thus from FIG. 4, the reflected signal is 23 dB plus the effective F/B ratio of 17 dB for a total of 40 dB absorber reflectivity.

The differential propagation losses in the test region can be estimated by comparing the data run with the probe pointed toward the source and then rotated 180 degrees toward the short circuit termination.

To minimize ambiguities in the data, it is recommended that an omnidirectional probe be used for low performance absorbers (less than 20 dB) and directional antennas with finite (10-20 dB) F/B ratios be used for higher performance materials.

TEST RESULTS

Two versions of the test system have been built. A small unit 2 ft by 2 ft for evaluating standard-sized absorbers down to 600 MHz and a larger system 10 ft by 10 ft by 35 ft long. This unit was developed to measure large absorbers (up to 9 ft long) from 140 MHz to 1000 MHz.

Above the low frequency cutoff, the bandwidth of the probe and source antennas determine the operating range of the system since the absorber lined horn is inherently broadband.

2'×2' Test System

The 2'×2' RF Absorber Test System was constructed with the square portion of the horn three feet long and the tapered section 4 feet in length. Four inch, high loss, wedge absorbers are used in the square section and flat absorber in the tapered section.

The source antenna consists of a broadband dipole fed with a ferrite balun for the 600-1500 Mhz frequency range. An LPA was used at the higher frequencies. Two LPA antennas covering the 600 MHz to 12 GHz frequency range were used as probe antennas. Some experiments were conducted with a second broadband dipole as a probe antenna. The bulk of the measurements were conducted in the 1000 to 1500 MHz range due to the availability of equipment.

The instrumentation used with this test system consists of the equipment illustrated in the block diagram given in FIG. 6.

The 10 ft by 10 ft Rf Absorber Horn Test System consists of a square section 15 ft long, driven by a tapered section 20 ft long. The test system was used to develop a new line of low frequency high performance absorbers optimized for operation at 100 MHz.

The source antenna utilized for the low frequency evaluation is a specially designed broadband dipole with a ferrite power divider for use from 100 MHz to 500 MHz. A lightweight LPA antenna was also constructed for use as a probe antenna. In order to keep the motion of the probe as smooth as possible so that very small VSWR'S (thus high absorption measurements) could be made, a custom designed carriage was constructed with one inch centerless ground rails and self aligning linear bearings was used. Proper construction of the probe mechanism proved to be paramount in obtaining repeatable data.

The instrumentation used with this low frequency test system is illustrated in FIG. 7.

A series of measurements conducted in the chamber is illustrated in FIGS. 8 through 15. FIG. 8 is the short circuit data at 200 MHz with a ripple of 7 dB indicating an effective F/B of 8.5 dB.

FIG. 9 is the absorber test data corresponding to FIG. 8 with a ripple of 0.5 dB which from FIG. 4 yields a signal level of −32 dB. When added to the −8.5 dB, F/B of the probe results in an absorber reflectivity of −40.5 dB. The dip to the far right of the chart is not evaluated due to it being very close to the tips of the absorbers being tested.

FIG. 10 is the short circuit data at 300 MHz utilizing the 100-500 MHz antenna. The ripple of 30 dB indicates a very poor effective F/B ratio of only 2 dB.

FIG. 11 is the absorber test data corresponding to FIG. 10, with a ripple of 0.5 dB or −32 dB signal level, which, added to the 2 dB yields a measured reflectivity of −34 dB.

Repeating the above measurement using a 300-1800 MHz antenna, it also showed a similar F/B ratio of 4 dB as illustrated in FIG. 12. The absorber measurement was also repeated and the result is recorded in FIG. 13. A 0.6 dB ripple was the result indicating a −30 dB level or a total of −34 dB for the absorber reflectivity. This demonstrates the excellent repeatability of the test system.

Figure 14:
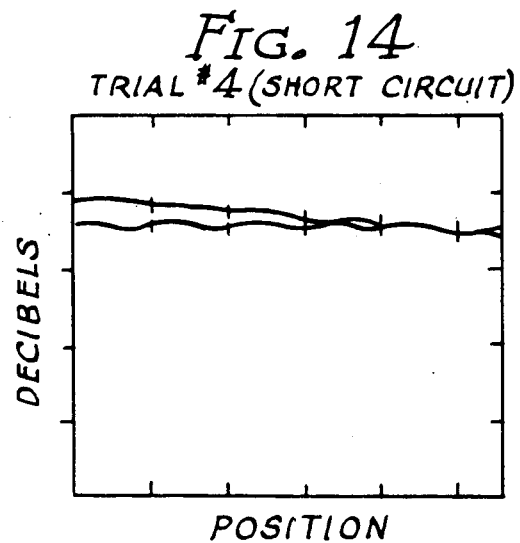
Figure 15:
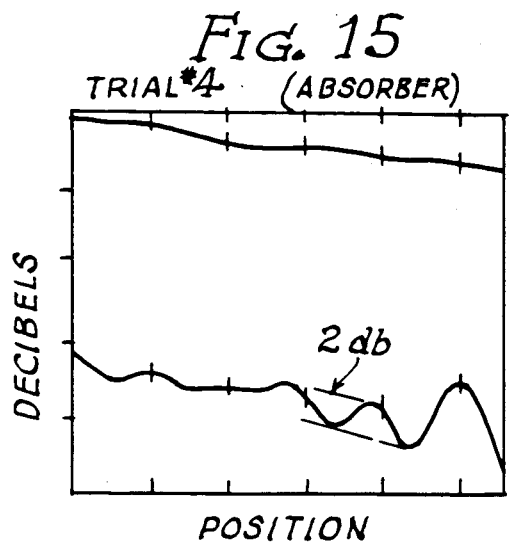

FIG. 14 is the short circuit data at 460 MHz with an effective F/B ratio of 21 dB. FIG. 15 is the absorber data illustrating a 2 dB ripple or −19 dB signal level, which, when added to the F/B ratio, yields an absorber reflectivity of −40 dB.

These tests were performed at normal incidence and axial alignment of the probe antenna. To round out the data, each of the absorber tests should ideally be repeated twice, once at −10° from axial alignment, and the other at +10°. Recording of the standing wave and calculation of the reflectivity would proceed in both incidences just as with the axial alignment condition. The three results can then be averaged, such that the overall result is a fairly complete, and repeatable, measurement of the reflectivity of any specimen RF absorber at low frequencies.

I claim:

1. A method of measuring the reflectivity of a test sample RF absorber using a test chamber having a longitudinal axis and comprising a flared section having a small source end housing a source antenna and flaring to a large end, and a substantially uniform section of uniform diameter extending from the large end of said flared section to its terminal end, said method comprising the following steps:
   (a) with said terminal and terminating in a short circuit, driving said source antenna to create a standing wave in said test chamber;
   (b) moving a directional probe antenna which is axially aligned with said chamber and directed toward said terminal end, along the axis of said chamber;
   (c) recording the varying amplitude of the standing wave received by said probe antenna as a function of distance travelled along said axis to produce a short circuit ripple;
   (d) measuring the peak-to-peak amplitude of said short circuit ripple, and comparing the resulting measurement to a ripple amplitude versus signal level chart to derive a short circuit reflected signal level in decibels;
   (e) repeating steps (a) through (d) except instead of said terminal end terminating in a short circuit, covering said short circuit with said test sample RF absorber, such that the signal level derived from said ripple amplitude versus signal level chart is an absorber reflectivity signal level in decibels; and,
   (f) adding said short circuit reflected signal level and said absorber reflectivity signal level to yield a figure for reflectivity of said absorber in decibels.

2. A method according to claim 1 wherein steps (a) through (f) are repeated, by with said probe antenna deviating from axial alignment with the terminal end of said chamber on the order of 10 degrees in a first direction.

3. A method according to claim 2 wherein steps (a) through (f) are repeated with the probe antenna deviating from axial alignment with said terminal end of said chamber on the order of 10 degrees in the opposite direction from said first direction.

4. A method according to claim 1 wherein said flared section of said chamber is of length on the order of two wave lengths of the frequency at which said source antenna is to be driven, and said substantially uniform section of uniform diameter is square and on the order of one wave length on a side and 1.5 wave lengths long.

5. A method according to claim 4 wherein said chamber is interiorly lined with a high loss RF absorber material.

* * * * *